United States Patent [19]

Atsumi et al.

[11] 4,209,525

[45] Jun. 24, 1980

[54] IMIDAZOLE ACETIC ACID DERIVATIVES

[75] Inventors: Toshio Atsumi, Ashiya; Yuzo Tarumi, Nishinomiya; Takao Kiyohara, Takarazuka, all of Japan

[73] Assignee: Sumitomo Chemical Company, Limited, Higashi, Japan

[21] Appl. No.: 971,826

[22] Filed: Dec. 19, 1978

[30] Foreign Application Priority Data

Jan. 6, 1978 [JP] Japan .................................. 53-662

[51] Int. Cl.² .................. A61K 31/415; C07D 233/90
[52] U.S. Cl. ................................. 424/273 R; 548/301
[58] Field of Search ..................... 548/301; 424/273 R

[56] References Cited

U.S. PATENT DOCUMENTS 4,140,788  2/1979  Atsumi et al. ...................... 548/301

OTHER PUBLICATIONS

Atsumi et al., Chem. Abst. 1977, vol. 86, No. 106582g.

Shaw et al., Chem. Abst. 1960, vol. 54, columns 554–556.

*Primary Examiner*—Natalie Trousof
*Attorney, Agent, or Firm*—Wenderoth, Lind & Ponack

[57] ABSTRACT

Imidazole derivatives represented by the formula:

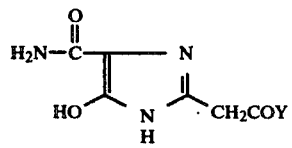

wherein Y is a hydroxy group, a lower alkoxy group or an amino group, and their non-toxic, pharmaceutically acceptable salts, which have a potent immunostimulating activity and are useful for the immunostimulatory therapy of various diseases, and their preparation and use.

2 Claims, No Drawings

IMIDAZOLE ACETIC ACID DERIVATIVES

The present invention relates to novel imidazole derivatives useful as an immunostimulant and their preparation and use.

It is known that the aglycone of Bredinin, 4-carbamoylimidazolium-5o-olate, shows a potent immunosuppressive activity as well as Bredinin. The inventors of the present invention have studied on biological properties of various imidazole derivatives and found that novel imidazole derivatives having the formula (I) as defined below and their non-toxic, pharmaceutically acceptable salts have a potent immunostimulating activity and are useful for the immunostimulatory therapy of various diseases such as Collagen diseases, infectious diseases and tumors and for the prevention of such diseases.

Imidazole derivatives provided by the present invention are represented by the formula:

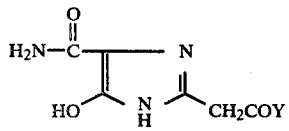

(I)

wherein Y is a hydroxy group, a lower alkoxy group or an amino group. As used herein, the term "lower alkoxy group" means an alkoxy group having one to four carbon atoms such as methoxy, ethoxy, n-propoxy, isopropoxy, n-butoxy, isobutoxy, t-butoxy and the like.

The imidazole derivatives of the present invention can be prepared by the following methods.

Thus imidazole derivatives of the formula:

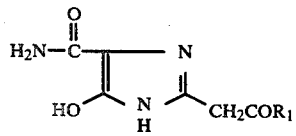

(I-a)

wherein $R_1$ is a lower alkoxy group or an amino group, and their salts can be prepared by reacting aminomalonamide with an imide ester of the formula:

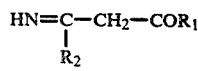

(II)

wherein $R_1$ is as defined above and $R_2$ is a conventional imide ester moiety such as phenoxy, benzyloxy, substituted benzyloxy (e.g., m- or p-nitrobenzyloxy), alkoxy, benzylthio and the like, or its salt (preferably hydrochloride), in an organic solvent, preferably at a temperature of 0° to 100° C. Examples of preferred solvents to be used are alcohols (e.g., methanol, ethanol, and the like), ethers(e.g., tetrahydrofuran, dioxane, ethyl ether, dimethoxyethane, and the like), polar solvents (e.g., dimethylformamide, acetonitrile, dimethylsulfoxide, acetamide, and the like), aromatic hydrocarbons (e.g., benzene, toluene, xylene, and the like) and halogenated hydrocarbons (e.g., carbon tetrachloride, dichloroethane, chloroform, dichloromethane, and the like). Among them, particularly preferable solvent is methanol. The reaction can preferably be conducted at a temperature of 0° to 100° C. and especially, the compound of the formula (I-a) can be obtained in a good yield when the reaction is conducted in methanol under reflux for one to several hours.

The imide ester of the formula (II) can be prepared from a cyanoacetic acid derivative of the formula:

$$NC-CH_2-COR_1 \quad (IV)$$

wherein $R_1$ is as defined above, in a conventional way (Pinner and Oppenheimer, Ber., 28, 478, (1895)).

The imide ester of the formula (II) wherein $R_1$ is a lower alkoxy is preferably used in preparing the compound of the formula (I-a).

The imidazole derivatives of the formula (I-a) can also be prepared by reacting aminomalonamide with an ortho ester of the formula:

$$(R_3O)_3CCH_2COR_1 \quad (III)$$

wherein $R_1$ is as defined above and $R_3$ is a lower alkyl group. This reaction can be carried out in the same manner as above.

The imidazole derivative of the formula (I) wherein Y is a hydroxy group can be prepared by hydrolyzing the imidazole derivatives of the formula (I) wherein Y is a lower alkoxy group in the presence of an alkali.

The imidazole derivative of the formula (I) wherein Y is a hydroxy group obtained as above can easily be converted into the form of their pharmaceutically acceptable salts by treating them with, for example, sodium hydroxide, potassium hydroxide, sodium carbonate, potassium carbonate, sodium bicarbonate, potassium bicarbonate and the like in a conventional way.

The imidazole derivatives of the present invention may be brought into a suitable dosage unit form in a known method. For example, they may be formulated with a suitable carrier into tablets or capsules with a daily dosage of 25 to 500 mg or into injections.

In the following, immunostimulating activities of the imidazole derivative of the present invention are described. The immunostimulating activity against the humoral immunity was determined according to Cunningham's method [A. J. Cunningham, Immunology 14, 599, (1968)].

Table I

| Compound | Immunostimulating effect on mouse | | |
|---|---|---|---|
| | mg/kg/day P.O. | Effect PFC/spleen × $10^{-4}$ | Enhance (%) |
| <br> | 25 | 82.75 ± 11.42 | 59.9 |
| | 50 | 82.75 ± 5.57 | 59.9 |
| | 100 | 80.13 ± 5.76 | 54.8 |
| | 200 | 67.75 ± 5.31 | 30.9 |

Table I-continued

| Compound | Immunostimulating effect on mouse | | |
|---|---|---|---|
| | mg/kg/day P.O. | Effect PFC/spleen × 10⁻⁴ | Enhance (%) |
| Control | | 51.75 ± 7.49 | — |

A sheep red blood cell preparation (SRBC) was injected intraperitonealy in mice and the compounds were administered orally once a day on days 0, 1, 2, 3. The plaque forming cell (PFC) number was measured on day 4 by Cunningham method.

Although, in the previous description, the structure of the imidazole derivatives of the present invention is given in the enol form as represented by the formula (I). The imidazole derivatives of the present invention may exist in the keto form as represented by the formula,

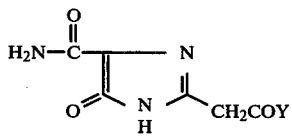
(I-K)

wherein Y is as defined above. It is to be understood that the imidazole derivatives both in the enol form and in the keto form are within the scope of the present invention.

The following examples are given to illustrate the present invention more precisely, but it is not intended to limit the present invention thereto.

EXAMPLE 1

Ethyl iminoethoxycarbonylacetate hydrochloride (49.59 g) and aminomalonamide (24.7 g) were added to anhydrous methanol (500 ml) under ice-cooling while stirring. After stirring was continued for 1 hour, the mixture was refluxed for 4½ hours and then cooled with ice. The precipitated crystals were collected, washed with ethanol and diisopropyl ether and dried under vacuum to give ethyl 4-carbamoyl-5-hydroxy-1H-imidazole-2-acetate (32.69 g, 72.7%). m.p. 241°–241.5° C. (decomposition)

Elemental analysis: Calculated for $C_8H_{11}O_4N_3$ (213.19)—C; 45.07%, H; 5.20%, N; 19.71%. Found—C; 44.9%, H; 5.2%, N; 19.4%.

Using the same procedures as above, the following compounds were obtained:

Methyl 4-carbamoyl-5-hydroxy-1H-imidazole-2-acetate, m.p. 240.5°–241° C. (decomposition)

n-Propyl 4-carbamoyl-5-hydroxy-1H-imidazole-2-acetate, m.p. 228°–228.5° C. (decomposition)

Isopropyl 4-carbamoyl-5-hydroxy-1H-imidazole-2-acetate, m.p. 244°–244.5° C. (decomposition)

n-Butyl 4-carbamoyl-5-hydroxy-1H-imidazole-2-acetate, m.p. 217.5°–220.5° C. (decomposition)

Isobutyl 4-carbamoyl-5-hydroxy-1H-imidazole-2-acetate, m.p. 231.5°–232° C. (decomposition)

EXAMPLE 2

To 300 ml of anhydrous methanol was added 0.92 g of sodium and then 4.26 g of ethyl 4-carbamoyl-5-hydroxy-1H-imidazole-2-acetate was added thereto under ice-cooling. 5 minutes thereafter, the mixture was warmed to a room temperature and stirred for 15 minutes. The resulting mixture was concentrated under vacuum and the residue was dissolved into 100 ml of water. After addition of 120 ml of 1 N aqueous hydrochloric acid, the precipitated crystals were collected, washed with ethanol and diisopropyl ether, and dried to give 3.04 g of 4-carbamoyl-5-hydroxy-1H-imidazole-2-acetic acid, m.p. 299° C. (decomposition). Yield: 82.2%.

Elemental analysis: Calculated for $C_6H_7O_4H_3$ (185.14)—C; 38.92%, H; 3.81%, N; 22.70%. Found—C; 38.8%, H; 4.0%, N; 22.5%.

EXAMPLE 3

Ethyl imino α-carbamoylacetate hydrochloride (5.98 g) and aminomalonamide (3.51 g) were added to anhydrous methanol (80 ml) under ice-cooling while stirring. After stirring for ½ hour, the mixture was refluxed for 2 hours and then cooled with ice. The precipitated crystals were collected, washed with ethanol and diisopropyl ether and dried under vacuum to give 4-carbamoyl-5-hydroxy-1H-imidazole-2-acetamide (3.88 g, 70.3%), m.p. 270° C. (decomposition).

Elemental analysis: Calculated for $C_6H_8O_3N_4$ (184.16)/½H₂O—C; 38.20%, H; 4.54%, N; 29.70%. Found—C; 38.1%, H; 4.3%, N; 29.6%.

What is claimed is:

1. A compound of the formula,

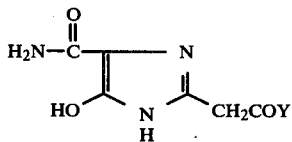

wherein Y is hydroxy, lower alkoxy or amino, and its pharmaceutically acceptable salts.

2. A pharmaceutical composition useful as an immunostimulant which comprises an immunostimulatory amount of a compound of claim 1 and a pharmaceutically acceptable carrier.

* * * * *